United States Patent
Jørgensen et al.

(10) Patent No.: US 10,627,319 B2
(45) Date of Patent: Apr. 21, 2020

(54) SAMPLING APPARATUS FOR USE IN EXPLOSIVE ENVIRONMENTS, A DRYER COMPRISING SUCH A SAMPLING APPARATUS, AND METHOD OF ESTIMATING THE FLOWABILITY OF A SAMPLE

(71) Applicant: GEA Process Engineering A/S, Søborg (DK)

(72) Inventors: Thomas Kniep Jørgensen, Kolding (DK); Anders Sehested, Roskilde (DK); Esben Krauthammer, København N (DK)

(73) Assignee: GEA Process Engineering A/S (DK)

( * ) Notice: Subject to any disclaimer, the term of this patent is extended or adjusted under 35 U.S.C. 154(b) by 230 days.

(21) Appl. No.: 15/580,329

(22) PCT Filed: Jun. 9, 2016

(86) PCT No.: PCT/DK2016/050177
§ 371 (c)(1),
(2) Date: Dec. 7, 2017

(87) PCT Pub. No.: WO2016/198078
PCT Pub. Date: Dec. 15, 2016

(65) Prior Publication Data
US 2018/0172559 A1    Jun. 21, 2018

(30) Foreign Application Priority Data
Jun. 9, 2015    (DK) ................................ 2015 70353

(51) Int. Cl.
*G01N 1/20*    (2006.01)
*G01N 21/01*    (2006.01)
(Continued)

(52) U.S. Cl.
CPC ............. *G01N 1/20* (2013.01); *G01N 1/2035* (2013.01); *G01N 21/01* (2013.01); *G01N 21/85* (2013.01);
(Continued)

(58) Field of Classification Search
CPC .......... G01N 1/30; G01N 21/01; G01N 21/85; G01N 33/04; G01N 1/2035
See application file for complete search history.

(56) References Cited

U.S. PATENT DOCUMENTS

| 5,385,058 | A | 1/1995 | Krauss |
| 5,563,384 | A | 10/1996 | Marlow et al. |

(Continued)

FOREIGN PATENT DOCUMENTS

| CN | 201302529 Y | 9/2009 |
| DE | 19909437 A1 | 9/2000 |

(Continued)

OTHER PUBLICATIONS

Search Report for DK PA 2015 70353.
Lumay et al., "Measuring the Flowing Properties of Powders and Grains", Powder Technology, vol. 224, Feb. 2012, pp. 19-27.
Sehested, "Advanced Process Control", Danish Dairy & Food Industry, vol. 24, pp. 12-13.

*Primary Examiner* — Jamel E Williams
(74) *Attorney, Agent, or Firm* — Condo Roccia Koptiw LLP

(57) ABSTRACT

The invention relates to a sampling apparatus for use in explosive environments comprising particles of a mean size of up to 500 µm, the sampling apparatus comprising a displaceable arm having a sample container, which displaceable arm has a first position where the sample container is inserted into a first zone for collecting a sample of particles into the sample container, and a second zone where the displaceable arm is outside the product stream, the second zone being contained in a housing with an opening for the displaceable arm. The sampling apparatus has an interface
(Continued)

between the first and the second zone, which interface is selected from the list consisting of a closable member, a gate valve or an air knife. The invention also relates to a dryer comprising a drying chamber and a sampling apparatus of the invention. In a further aspect the invention relates to a method of estimating the flowability of a sample of organic particles.

23 Claims, 14 Drawing Sheets

(51) Int. Cl.
    *G01N 21/85*      (2006.01)
    *G01N 33/04*      (2006.01)
    *G01N 1/10*      (2006.01)

(52) U.S. Cl.
    CPC ..... *G01N 33/04* (2013.01); *G01N 2001/1018* (2013.01); *G01N 2021/0193* (2013.01)

(56) References Cited

U.S. PATENT DOCUMENTS

| | | | |
|---|---|---|---|
| 10,274,404 B1* | 4/2019 | Novosselov | G01N 1/24 |
| 2005/0188774 A1* | 9/2005 | Stoffel | F17D 3/10 |
| | | | 73/863.86 |
| 2013/0312547 A1* | 11/2013 | Jorgensen | G01N 1/20 |
| | | | 73/864.51 |

FOREIGN PATENT DOCUMENTS

| | | |
|---|---|---|
| DK | 177236 B1 | 7/2012 |
| EP | 0520472 A2 | 12/1992 |
| EP | 0710828 A1 | 5/1996 |
| EP | 2243015 A2 | 10/2010 |
| GB | 2150917 A | 7/1985 |
| GB | 2220250 A | 1/1990 |
| WO | WO 2009/010574 A2 | 1/2009 |

* cited by examiner

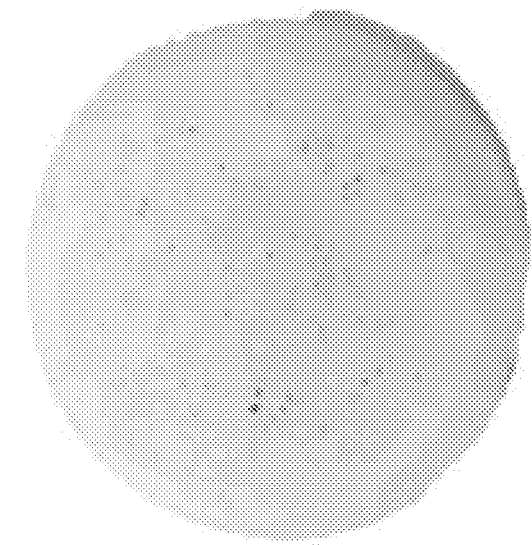
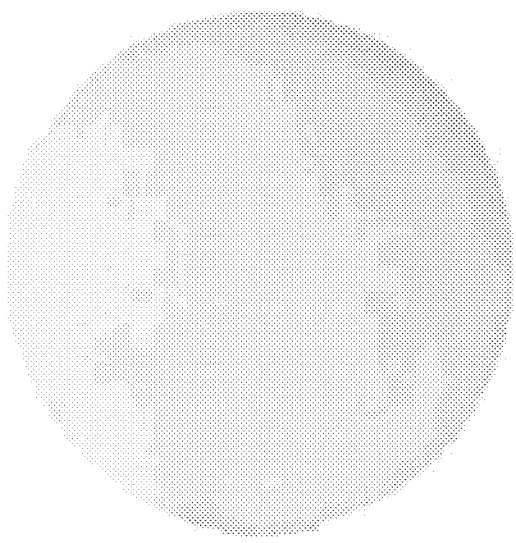
Fig. 7

SAMPLING APPARATUS FOR USE IN EXPLOSIVE ENVIRONMENTS, A DRYER COMPRISING SUCH A SAMPLING APPARATUS, AND METHOD OF ESTIMATING THE FLOWABILITY OF A SAMPLE

CROSS REFERENCE TO RELATED APPLICATIONS

This application is the National Stage Entry under 35 U.S.C. § 371 of Patent Cooperation Treaty Application No. PCT/DK2016/050177, filed 9 Jun. 2016 which claims the benefit of Danish Patent Application No. PA 2015 70353, filed 9 Jun. 2015, the contents of which are hereby incorporated by reference in their entirety.

FIELD OF INVENTION

The present invention relates to a sampling apparatus for use in explosive environments comprising particles of a size of up to about 500 µm, the sampling apparatus comprising a displaceable arm having a sample container, which displaceable arm has a first position where the sample container is inserted into a first zone for collecting a sample of particles into the sample container, and a second zone where the displaceable arm is outside the product stream, the second zone being contained in a housing with an opening for the displaceable arm. The invention furthermore relates to a dryer comprising the sampling apparatus and to a method of estimating the flowability of a sample of particles.

BACKGROUND OF THE INVENTION

The field of drying powders is concerned with specific problems that may occur due to the potential flammability in form of dust explosions of such powders, and a drying process should be carefully monitored to estimate the risk of explosions/fires in the dryer.

DK177236B1 discloses an apparatus for online sampling from a product stream, where the sampling is carried out in an ongoing manner by placing a container with an opening directly into a product stream, wherein the flowing product is collected in said container for determining one or more physical conditions, for example weight relative to volume, humidity, size and/or colour. The apparatus comprises at least one displaceable container, and means for displacing the container.

EP2243015B1 discloses a device for sampling from a product stream, where the sampling is carried out in an ongoing manner and wherein the product is collected in a sample container to determine physical conditions, for example weight relative to volume.

A commercial sampling apparatus known as the POWDEREYE™ is also known.

The known devices for sampling have in common that they are not suited for taking samples in explosive environments where there can be a mixture of air and flammable substances under atmospheric conditions, which if ignited could spread in the remaining product. The flammable material may for example be in the form of gasses, vapour, mist and/or dust.

The known devices for sampling thus do not satisfy the safety requirements for use in explosive atmospheres, as none of the devices include explosion zones.

Within the field of powder processing it is further of interest to estimate the flowability of a sample of particles. Estimation of the flowability of a sample of particles has been suggested by Lumay, Boschini, Traina, Bontempi, Remy, Cloots & Vandewalle (2012, *Powder Technology*, 224: 19-27). The method involves placing a sample of particles in a cylinder, placing a light object on top of the sample to keep it flat, and letting the cylinder go through a number of cycles of lifting the cylinder and letting it fall the same distance, and measuring the height of the sample after each fall. The method is not suited for integration into an apparatus for on-line or in-line monitoring of a process.

SUMMARY OF THE INVENTION

With this background, it is therefore an object of the present invention to provide a sampling apparatus for use in an explosive environment. Particles of an organic material can reach a point of dryness, e.g. during the drying in a vertical dryer, where they burn easily. When the particles are within a certain range of sizes, e.g. up to 500 µm in diameter, they generally have a sufficiently large specific surface area, which coupled with their distribution in dry air create a risk of fires or even explosions, which can happen by a single spark caused by static electricity or from an electrical installation in contact with the stream of particles or by self-ignition in case of heating and/or exothermal deposits It is an object of the present invention to provide an apparatus for collecting samples from zones where there is a risk of explosions, thus satisfying the requirements of, for example ATEX (ATmosphères EXplosives) and/or other standards in the field, such as IECEx and HAZLOC.

It is also an object of the invention to be able to at least perform one or more of a number of measurements, such as density, detection of the content of fat, protein and/or water, colour coding, scorched particles, and particles size.

It is a further object of the invention to be able to perform a verification of the conducted measurements, for example, density and particle size.

It is furthermore an object of the invention to provide a method of estimating the flowability of a sample of particles.

In a first aspect of the invention, these and further objects are obtained by a sampling apparatus having an interface between the first and the second zone, which interface is selected from the list consisting of a closable member, a gate valve, an air knife, a lock or an access gate filled by the displaceable arm.

According to a first aspect of the invention the above object is achieved with a sampling apparatus for use in explosive environments. In particular the sampling apparatus can withdraw a sample of particles from a stream of particles, e.g. a product stream, which stream of particles represents the "explosive environment". The sampling apparatus has an interface between the first and the second zone, which interface prevents a fire from spreading from the second zone to the first zone, or vice versa. The interface may also be referred to as a zonal division. The first zone may also be referred to as an "explosion zone". In this context an explosion zone means any zone or area where there is a potentially explosive atmosphere. In contrast to explosion zones there are no-explosion zones, or "non-zones", which in this context means zones and areas where there is low or no explosion hazard. Only the first zone is an explosion zone and the interface between the first and the second zone will also ensure that any further zone defined in the sampling apparatus is also a no-explosion zone.

The stream of particles will typically be located in any section of a dryer or in a section downstream, with respect to the flow of particles, of the drying section, e.g. the particles may be in a spray dryer, fluid bed, flash dryer, ring dryer, spray dryer with integrated or external fluid bed, etc. In general, a dryer has an inlet for a liquid feed, e.g. at the top of a vertical dryer, where a liquid feed enters the dryer and meets a stream of dry, hot air so that droplets of feed will fall down inside the dryer and liquid will be removed from the droplets resulting in formation of substantially dry particles. The liquid feed may be a slurry or suspension of particles or a solution capable of forming particles upon removal of the solvent. In a specific embodiment, the stream of particles to be sampled is in an outlet duct of a dryer.

In a specific embodiment the first zone is classified as "zone 20" according to the A-tex guideline 2014/94/EU, and the second zone is classified as "zone 22" according to the A-tex guideline 2014/94/EU. If further zones are present in the sampling apparatus these will preferably be isolated from the second zone to be classified as "safe zones".

E.g. milk powders represent a flammable substance due to the small size of the particles in the stream, and the sampling apparatus of the invention is suited for taking samples from a milk powder during the drying of such powders. An explosion may occur in a relevant powder as a dust explosion, e.g. caused by a spark, or from self-ignition in an exothermic reaction. The sampling apparatus of the invention is thus suited for withdrawing particles from a vertical dryer or from a vertical powder leading duct for subsequent analysis. The sampling apparatus comprises a displaceable arm having a sample container. The displaceable arm has a first position where the sample container is inserted into the product stream for collecting a sample into the sample container and a second position where the displaceable arm, in particular the part of the displaceable arm with the sample container, is outside the product stream, where the risk of explosion is low. The first position may also be referred to as a first zone, and the second position may also be referred to as a second zone or a "measuring well".

The second zone is contained in a housing with an appropriate opening for the displaceable arm, and the second zone may thus be confined by any appropriate division from the first zone. For example, the first zone may be separated from the second zone by a wall or the like with an opening, e.g. a duct, through which the displaceable arm can pass so as to enter the first zone from the second zone. The opening together with any appropriate device for preventing a fire from spreading between the zones represent the interface. The opening is generally sized to fit the displaceable arm.

The interface may comprise a closable member, e.g. a door, such as a sliding door or an Iris diaphragm, e.g. with 3 to 20 blades, or a valve, such as a gate valve, or the interface may comprise an air knife. In this context an air knife means a sheet of air using any suitable air or gas, e.g. nitrogen, a noble gas such as argon or neon, or air of atmospheric composition, covering the opening. In particular, the air knife may be provided as a uniform sheet of air, e.g. air flowing in a laminar pattern. The air knife may be created by any means as desired. For example, the air knife may be created by compressed air flowing through a thin nozzle, e.g. with a linear shape, designed to create the sheet, or curtain, of air between the first and the second zone. The nozzle may lead the air in a straight line or in a rotational direction. The air knife may also comprise an outlet nozzle, e.g. with a linear shape, for removing air from the inlet nozzle or inlet nozzles of the air knife. One or more outlet nozzles are especially relevant when the air knife employs a laminar flow of air. In a further embodiment the air knife comprises a plurality of inlet nozzles surrounding the opening between the first and the second zones, e.g. the nozzles are located in a duct between the first and the second zone. Thereby a flow of air into the opening from the nozzles will prevent that particles can pass between the first and the second zone unless they are in the sample container. Furthermore, the force can be increased as the surrounding air is drawn along by the compressed air flow when the latter exits the nozzle. In an embodiment the displaceable arm is pulled through the air knife which thus surrounds the entire displaceable arm. For example, the air knife may be activated when the displaceable arm, e.g. including the sample container, has passed the nozzle(s) of the air knife. In a further embodiment the interface between the first and the second zone comprises both a closable member and an air knife.

The sampling apparatus makes it possible to determine at least one characteristic of a product, such as density, residual moisture of the particles, particle size, scorched particles and/or colour. In a preferred embodiment the sampling apparatus monitors the risk of an explosion occurring in the first zone based on the analysed characteristics; the sampling apparatus may comprise a device for providing an alarm when the risk of fire reaches a predetermined level so that the dryer can be shut down to prevent a fire. The integrated monitoring of the powder thus allows that the drying process can be controlled more efficiently. For example, in a traditional process for the manufacture of a whole milk powder the milk powder is treated to provide an expected moisture content of 2.5% but underlying large variations, but with a sampling apparatus of the present invention the milk powder can be monitored to reach a moisture content closer to the required limit of 3% to 4%, which in turn provides a saving in the energy requirement, and moreover the milk powder will be of a higher quality since it contains fewer scorched particles. These advantages are not limited to milk powders, since the same considerations apply for other powders.

The sampling apparatus is especially suited for use in a vertical dryer for producing a powder with a mean particle size in the range of up to about 500 µm, such as e.g. in the range of 10 µm to 200 µm, for all products within food, pharmaceuticals, dairy, chemical, agro-chemical, energy, biotechnology, healthcare and many more such as a milk powder, a coffee whitener, an infant formula, a coffee powder, a pharmaceutical, a chemical etc.

The sampling apparatus, and in particular the displaceable arm and the sample container, is preferably constructed from antistatic materials, such as antistatic metal and antistatic polymer materials. For example acid-proof stainless steel, Teflon™ (PTFE), TCP (Trivalent chromium passivation) treated aluminium or conductive/electrically conductive plastics as anti-static polypropylene (PP) or antistatic polyethylene (PE) may be used. Thereby especially the sample container of the apparatus can divert or prevent static electricity, which may otherwise occur in a flow of dry powders. Regardless of the material, any part of the sampling apparatus, and also of a dryer in which the sampling apparatus is installed, may be electrically connected to the ground in order to further reduce the risk of fires caused by static electricity.

In the context of the invention a sample container means a sample extraction container, which may be designed and integrated in the displaceable arm or which may be compounded with the displaceable arm. The sample container may for example be a cup mounted on the displaceable arm or integrated in the displaceable arm. The sample container may have any shape and size, e.g. volume, as desired. For example, the depth of the sample container, e.g. a cylindrical sample container, may be in the range of 2 cm to 15 cm. A cylindrical sample container may have a diameter in the range of 2 cm to 15 cm. For example the sample container may have a volume of about 50 ml. In another embodiment the sample container has a volume of about 200 ml. Regardless of the volume, the aspect ratio, e.g. the diameter compared to the depth of a cylindrical sample container, may also be chosen freely.

The housing may comprise devices for monitoring and adjusting the pressure in the second zone, e.g. relative to the pressure of the first zone. For example, the pressure in the second zone may be higher than the pressure in the first zone. By maintaining an excess pressure in the second zone dust cannot enter the second zone and create deposits or an explosive atmosphere in the second zone, and thereby explosions can be avoided using excess pressure. The same is relevant for any other zone in the sampling apparatus.

A sample collected by the sampling apparatus may be analysed for any physical or chemical characteristic, and in an embodiment the sampling apparatus comprises one or more devices for analysing, e.g. measuring, quantifying, etc., a physical or chemical characteristic, such as density, moisture, particle size, scorched particles and/or colour of collected a particulate sample. Thus, the sampling apparatus may be used for taking a sample and analysing it, and use of the apparatus generally involves the following steps:

moving the displaceable arm from the second position to the first position thereby inserting the sample container into a product stream, wherein a filling opening of the sample container faces the product stream thereby filling the sample container, moving the displaceable arm from the first position to the second position, e.g. while brushing off excess sample from the sample container, analysing at least one physical or chemical characteristic of the sample, moving the displaceable arm from the second position to the first position and inverting the sample container to empty it into the product stream, cleaning the sample container.

The sampling performed with the sampling apparatus may be performed at regular intervals, arbitrary intervals or at any interval as desired by an operator during a process of drying an organic powder. The sampling may thus follow an automatic scheme or the sampling may be performed manually or on demand.

In another embodiment the sampling apparatus further comprises a device for cleaning the sample container. The device may be operated manually or the device may be set to perform a cleaning operation following a set of predetermined instructions, which may also be referred to as an "automatic" cleaning. The device for cleaning the sample container may comprise at least one air nozzle pressurised with a medium, e.g. a gaseous inert medium, such as nitrogen or air, for flushing the sample container, e.g. after emptying the sample container. The device for cleaning the sample container may be integrated with the displaceable arm or it may be external to the displaceable arm. For example, the device for cleaning the sample container may have an air nozzle located in the first zone, i.e. in the product stream, below the site where the displaceable arm exits the second zone so that the air nozzle blows air up against the bottom of the interior side of the sample container when it is inverted, or at least away from the direction of the product stream and typically more than 90 degrees, whereby the air can be blown against the product stream. The device for cleaning the sample container may be fixed in the product stream or it may be displaceable in the sampling apparatus to follow the displaceable arm in order to clean the sample container, e.g. after emptying. In another embodiment the sampling apparatus has a further or alternative device for cleaning the sample container, which is located in the second zone for cleaning the sample container in the second zone, e.g. after emptying the sample into a verification tube. The device for cleaning the sample container thus makes it possible to clean the sample container when the content of the sample container has been emptied back into the product stream or into the verification tube, e.g. before the sample container is placed back into the product stream. The device for cleaning the sample container is particularly relevant for a sampling apparatus used in food manufacturing, in the food industry or in a pharmaceutical production with high requirements to the overall process hygiene, e.g. as part of a Cleaning In Place (CIP) procedure that may be an automatic CIP process.

In a specific embodiment the sampling apparatus comprises both a device for cleaning the sample container and also a vibrator for vibrating the sample container. The vibrator can be used during emptying and cleaning of the sample container, e.g. when the sample container is inverted and the oscillations loosen the sample from the sample container and contribute to an improved emptying of the sample container.

In an embodiment the sampling apparatus comprises a device for analysing a physical or chemical characteristic of the sample. In an embodiment the device can analyse the physical or chemical characteristic of the sample without contacting the sample. For example, the sampling apparatus may have a laser or a lamp for generating light of a desired wavelength, e.g. monochromatic wavelengths, or range of wavelengths, e.g. ultraviolet (UV), infrared (IR), near infrared (NIR) or visible light, or a device for generating sound of a relevant frequency or range of frequencies, e.g. ultrasound, and an appropriate sensors for detecting light and/or sound as well as a data processor capable of recording and interpreting a signal obtained from a sensor. For example, the sampling apparatus may comprise a laser scanner, a NIR scanner, a camera, a vision system etc. A laser scanner, a NIR scanner, a camera, and/or a vision system may comprise a data processor capable of recording and interpreting a signal obtained from a corresponding sensor.

A laser scanner can be employed, e.g. to examine the amount of powder in the sample container, e.g. if the sample container is full or empty, or how much sample is present in the sample container. In a specific embodiment the sampling apparatus has a laser and a detector, which together can measure the level of sample in the sample container. The level of sample in the sample container can also be referred to as the "height" of the sample.

A NIR scanner can be used to analyse e.g. the content of fat, protein and/or moisture of a sample in the sample container. Use of a NIR scanner to analyse the content of fat, protein and/or moisture of a sample is well known in the art and the specific procedure may be selected freely.

An ultrasound source may be used to separate agglomerated particles from each other. Separation of agglomerated particles is particularly useful for the embodiment where the sample cup is designed for analysis of particle size, e.g. where the sampling apparatus has a size sampling container.

When the sampling apparatus comprises a camera and an appropriate image analysis system, i.e. a vision system, with an optional light source, the vision system can be used to measure the number of colour deviating particles in the sample and compare it to the total number of particles and/or the number of particles without colour deviations from the expected colour. For example, particles of a milk powder should be white, and darker particles or particles with dark spots, which in this context are considered colour deviating particles, may indicate a risk of fire or explosion in the dryer, since such colour deviating particles typically represent scorched particles. For example, the vision system may employ the colour scheme CMYK (Cyan Magenta Yellow Key) or RGB (Red-Green-Blue) for image analysis where each pixel of an image receives a colour code thereby allowing comparison of the respective pixel codes in order to make a general colour code for the whole powder. Each particle may be represented by one or more pixels, and the amount or proportion of colour deviating particles may be presented as deviating pixels relative to the total number of pixels, or the amount or proportion of colour deviating particles may be presented as a particle based value. The vision system thus preferably comprises software capable of calculating and quantifying the colour deviations. The number of pixels recorded by the camera may be selected freely, and as may the shape or format of the recorded image. For example, the camera may record from 1000 pixels and up to $10^6$ pixels or more, e.g. 5000 pixels. In an embodiment the format of the picture is square, i.e. 1:1, and in another embodiment the picture is recorded in a 4:3 or 16:9 format. In a preferred embodiment the picture has a circular format and comprises from 10,000 pixels to 1,000,000,000 pixels. The vision system may comprise, in addition to an appropriate camera, a filter for controlling the light from a light source, e.g. to provide a monochromatic light or light of a range of wavelengths, and a filter for controlling the light entering the camera. Filters may likewise be used when the sampling apparatus has laser and an appropriate detector, e.g. for measuring fluorescence. The vision system may include all state of the art facilities/options available.

Thus, with a vision system it is possible to count the number of colour deviating particles, e.g. in a white milk powder. The colour deviating particles, when representing scorched particles, can constitute an expression of the risk of fire or explosion in a vertical dryer. The quantification of the colour deviating particles may therefore be used to generate a signal of alert for shutting down and cleaning the system in order to avoid a fire. In a specific embodiment the sampling apparatus comprises an alarm set to signal a risk of fire.

In a further aspect the invention relates to a method of quantifying colours in a surface of particles. When particles are extracted using the sample apparatus of the invention or a similar system not suited for extracting samples in an explosive environment the particles will be present in an uneven layer so that shadows caused by features in the uneven layer may be misinterpreted as having a different colour, e.g. a darker colour, from the actual colour of the particles thus creating a risk of "false positives" with respect to quantifying colour deviating particles. This problem is particularly relevant when quantifying colour deviating particles as "scorched particles" as discussed throughout this document. Thus, the invention also relates to a method of quantifying colours in a surface of particles, the method comprising the steps of:
  providing a sample of particles having a mean size distribution in the range of 10 μm to 500 μm in a sampling container,
  optionally scraping the surface of the particles,
  taking an image of the surface of the particles,
  recording colours of the pixels in the image according to a colour scheme,
  labelling pixels having a threshold value in the colour scheme,
  comparing the colours of the pixels surrounding the labelled pixels with colours of the labelled pixels,
  differentiating colour deviating particles from uneven features in the surface based on the comparison between the labelled pixels and the pixels surrounding the labelled pixels, and
  quantifying colour deviating particles in the surface.

The pixels surrounding the labelled pixels may have any suitable distance from the labelled pixels, e.g. from 1 to 100 pixels away from the labelled pixels.

The image is preferably taken vertically above the surface. The step of taking the image may comprise providing a light having a desired colour, e.g. a white light or light having a range of wavelengths. The colour scheme may be selected freely, e.g. an RGB scheme or a CMYK scheme.

The method advantageously allows true positive colour deviating particles to be differentiated from false positives in the surface. The method is preferably performed in a sampling apparatus of the invention, and any feature of any embodiment of the sampling apparatus is relevant for the method.

In an embodiment, e.g. when the sampling apparatus comprises a device for contact-free analysis of a physical or chemical characteristic of the sample, e.g. based on optical analysis, the sampling apparatus comprises a window with a window glass, which separates the second zone from the device for analysing a physical or chemical characteristic of the sample, e.g. the device for contact-free analysis of the sample. The window glass may be of any appropriate material, and it may have any thickness or size as desired. For example, the thickness or size may depend on what is necessary for the given surface area within the current measuring well. In a preferred embodiment the glass may be sapphire glass which is a crystal with a very wide optical transmission range from UV to IR. In addition, the sapphire glass is approved for food and is resistant to common acids and bases, it is moreover difficult to scratch because of its hardness and it is also resistant to high temperatures. In other embodiments the window glass is selected to provide a specific filter to filter out a desired range of wavelengths.

The sampling apparatus, e.g. the displaceable arm, may comprise a weighing cell, so that it is possible to weigh a sample, while at the same time also determining other characteristics of the sample. For example, the weighing cell may be integrated in or may be an integrated part of the displaceable arm.

In a certain embodiment the sample container has cylindrical sample container with a diameter and a depth of a ratio in the range of 1:10 to 1:1, e.g. 1:5 to 3:4.

In a preferred embodiment the sample container is rotatable around an axis transverse to the direction of the product stream from which a sample is collected. Thereby the sample container has a "filling position" where the opening of the sample container faces the product stream so that particles from the product stream will fill the sample container when the displaceable arm is in its first position. For example, the opening of the sample container may be horizontal, e.g. with respect to the opening of the sample container. When the sample container is inverted from the filling position, e.g. rotated more than 90°, the sample container will enter an "emptying position" where the sample container is emptied. In a specific embodiment the sample container also has a position for collecting a sample for particle sizing, i.e. a "particle sizing position". In the particle sizing position the sample container is rotated, e.g.

rotated in either direction, at an angle in the range of 5° to 85°, e.g. in the range of 30° to 60°, from the horizontal position. Thereby the sample container can only collect a limited amount of sample. When a limited amount of sample is collected in the sample container, it is possible to distribute the sample in the sample container so that individual particles can be distinguished. When the sample container has a particle sizing position it is preferred that the sampling apparatus has a vision system capable of analysing particle sizes. In a preferred embodiment the bottom of or the entire sample container has a colour in contrast to the colour of the particles to be analysed. For example, for the analysis of milk powders the sample container may have a black colour, or another dark colour complementary to the colour of the particles, e.g. blue. The amount of particles to be collected in a sample may be controlled by the time the displaceable arm is in the first position, so that the sample container is in the product stream for a short period of time. However, in a preferred embodiment the displaceable arm has a size sampling container, which has an aspect ratio, e.g. the diameter compared to the depth of the cut out in the removable arm making up the size sampling container, in the range of 100:1 to 10:1, e.g. 80:1 to 30:1. When a size sampling container is placed in the product stream in the particle sizing position, i.e. rotated at an angle in the range of 5° to 85°, e.g. in the range of 30° to 60°, compared to the horizontal position of the opening of the size sampling container, the volume available for the sample in the size sampling container is limited by the depth and the angle of the size sampling container, and when the displaceable arm is moved to its second position and the size sampling container is brought to a horizontal position the particles collected in the size sampling container will distribute over the surface of the bottom of the size sampling container, in particular if the size sampling container is vibrated by a vibrator or rotated to force the particles to slide. Thereby individual particles can be detected by the vision system and the sample can be analysed for particle sizes. In a preferred embodiment the displaceable arm has a size sampling container in addition to the sample container. In a particularly preferred embodiment the displaceable arm has a size sampling container in addition to the sample container, and the angle between the sample container and the size sampling container based on the axis transverse to the direction of the product stream is in the range of 20° to 80°, e.g. in the range of 30° to 60°. Thereby it is possible to simultaneously collect a sample for particle sizing in the size sampling container and a sample for other analyses in the sample container independently of the time for collection. However, if desired it is also possible to collect an appropriate sample in either the size sampling container or the sample container without collecting a sample in the other. When the sampling apparatus has a size sampling container it preferably also has a source of ultrasound.

In yet a further aspect the invention relates to a method of determining a size distribution of particles having a mean size distribution in the range of 10 µm to 500 µm. The method may in particular be performed in a sampling apparatus of the invention, e.g. a sampling apparatus having a size sampling container. The method of estimating a size distribution of particles having a mean size distribution in the range of 10 µm to 500 µm comprises the steps of:
providing a size sampling container having a bottom,
providing a sample of particles and distributing the particles in the bottom of the size sampling container,
taking an image of the bottom of the size sampling container,
recording colours of the pixels in the image according to a colour scheme,
labelling pixels having a threshold value in the colour scheme,
comparing the colours of the pixels surrounding the labelled pixels with colours of the labelled pixels,
differentiating particles from the bottom of the size sampling container based on the comparison between the labelled pixels and the pixels surrounding the labelled pixels,
estimating the sizes of the particles, and
counting the particles to determine a total number of particles.

In particular, the total number of particles is determined and from the sizes of the particles the particles may be classified according to size in order determine a size distribution of the particles.

The pixels surrounding the labelled pixels may have any suitable distance from the labelled pixels, e.g. from 1 to 100 pixels away from the labelled pixels.

The image is preferably taken vertically above the surface. The step of taking the image may comprise providing a light having a desired colour, e.g. a white light or light having a range of wavelengths. The colour scheme may be selected freely, e.g. an RGB scheme or a CMYK scheme. The method is preferably performed in a sampling apparatus of the invention, and any feature of any embodiment of the sampling apparatus is relevant for the method.

The sampling apparatus may comprise one or more actuators and/or one or more engines or motors that can move the displaceable arm between its first and second positions. The motor(s) and actuator(s) can thus move the sample container from the site where an analysis is performed, e.g. the measuring well, to the product stream for collecting a sample, and back. The motor(s) and actuator(s) may further be capable of inverting the sample container with respect to the direction of the product stream, e.g. to define a first position for collecting a sample and a second position for emptying the sample container. In a further embodiment the bottom of the sample container has a door or the like, which can be opened and closed using the motor(s) and actuator(s) so that the sample container can be emptied by opening the door.

The sampling apparatus may further comprise a machine housing, e.g. as part of the housing containing the second zone or as a housing separate from the housing of the second zone. The machine housing may define a separate zone, which may have its own classification with respect to the risk of explosion. The machine housing may comprise driving mechanisms for driving mechanical parts of the sampling, e.g. the motor(s) and actuator(s). Any actuator, motor or engine may be operated and controlled electrically, pneumatically, hydraulically or by any appropriate means.

In an embodiment the sampling apparatus comprises an instrument housing, which may be within the housing containing the second zone or the instrument housing may be separate from housing containing the second zone. Regardless of the position of the instrument housing relative to the housing containing the second zone, the instrument housing may be considered to define a third zone. The third zone may be of a different classification with respect to the risk of explosion than the first and the second zones, but it is preferably a safe zone with no risk of explosions. The instrument housing may contain any device of the sampling apparatus for analysing a physical or chemical characteristic of a sample, in particular the instrument housing can advantageously contain any device for analysing a physical or chemical characteristic without contacting the sample. For example a device for analysing a physical or chemical characteristic without contacting the sample can analyse the sample through a window glass as described above so that the instrument housing can be isolated from the second zone.

When a machine housing and an instrument housing, which are separate from each other, are employed, the two housings may be connected for example by a duct between the housings, and the two housings may be considered to be comprised in the same zone with the same excess pressure. The duct may comprise any sealing as desired if considered necessary.

The sampling apparatus may further comprise at least one seal e.g. between the instrument housing and the machine housing when present, which can be cleaned with a pressurised medium, e.g. gas or liquid, capable of separating the second zone from the machine housing. Thereby two zones can be separated from each other, e.g. according to classification with respect to the risk of explosion, whilst at the same time ensuring that the air/gas does not transfer material from the second zone to the third zone, which, in a preferred embodiment, is achieved by using a double lip seal that can be cleaned with an excess pressure from a pressurised medium, e.g. air or nitrogen. The seal is preferably kept clean by means of compressed air or nitrogen. In another embodiment labyrinth seals, other lip seals, or profile rings including O-rings are used.

Any wires or cables, e.g. for electricity, air, gasses, optical cables etc., such as wires or cables between the displaceable arm, e.g. to and from the sample container, and the second zone or the machine housing may be contained within the displaceable arm. Thereby wires and cables in the displaceable arm in the measuring well of the second zone cannot come into contact with powder and/or dust blown from the samples can, which minimises risk of explosion or fire from an occurring spark or a loose connection from an electrical wire.

In another embodiment the sampling apparatus further comprises a verification tube for transferring a sample in the sample container to an external site, e.g. for further analysis or for analysis using complementary analytical principles. The verification tube may be located between the measuring well of the second zone and an external verification unit. Thus, for example when the sample container has collected a sample, which has been analysed in the second zone, the sample container may be emptied into the verification tube. The verification tube may comprise a duct or the like through which the sample can be transferred to the external verification unit, e.g. using vacuum or another means for transferring the sample. In another embodiment the verification tube is a container that can be transferred to the external verification unit. The verification tube will preferably ensure that the sample is transferred to the external verification unit without modifying the conditions of the sample, e.g. with respect to surrounding humidity and pressure. For example, the verification tube may be sealed when the sample has been emptied into the verification tube, or the conditions, e.g. the surrounding humidity, pressure and temperature may be controlled.

The verification unit may be for example, an enclosed space in which the weight, volume (i.e. density) and the particle sizes of the sample can be verified as a control of the measurements of the sampling apparatus. This makes it possible to empty an extracted sample into a tube, wherein the tube, in a preferred embodiment, can take the sample to an enclosed space, wherein the sample can be verified, as a comparison of the measurements of the sampling apparatus.

In another embodiment the sampling apparatus comprises at least one vibrator. The vibrator may be of any design allowing the sample container to be vibrated, e.g. to loosen particles of a sample, which may adhere to the walls of the sample container. In the context of the invention a vibrator may also be referred to as an oscillator and the two terms may be used interchangeably. The vibrator may be integrated in the displaceable arm. In an alternative embodiment the vibrator is located externally to the displaceable arm, for example, in the verification tube, from which the vibrator can be pushed up to and brought into contact with the sample container, e.g. the bottom of the sample container, and vibrate the sample container and its content. The frequency of the vibrator may be chosen freely, e.g. to be in the range of 1 Hz to 100 kHz, e.g. in the range of 1 kHz to 50 kHz. The amplitude of the vibration will generally be up to about 2 mm, e.g. up to about 1 mm. In particular, the frequency, and also the amplitude, of the vibrator may be adjusted individually for different products, so that a desired outcome may be achieved.

The sample container may be vibrated in any position of the displaceable arm, e.g. in the first position or in the second position, and when the sample container is in the first position for collecting a sample and/or in the second position for emptying the sample container. Thus, the vibrator can vibrate the sample container to ensure that particles adhering to the walls of the sample container are loosened, e.g. when the sample container is emptied into the product stream or into the verification tube. In another embodiment the sampling apparatus has a vibrator to vibrate the sample container in the second zone so that it possible to vibrate the sample in the sample container thereby compacting the sample. The sample after such compaction may be referred to as a "tapped" sample, and the density of this sample is correspondingly the "tapped density". Likewise, the density of a sample recorded before vibration may be referred to as the "bulk density".

When the sampling apparatus comprises a vibrator capable of vibrating the sample container in the second zone it is preferred that the displaceable arm also comprises a weighing cell for weighing the sample. Thereby it is possible to measure the tapped density of the sample.

In a specific embodiment the sampling apparatus comprises a distance sensor, e.g. based on light, such as a laser, or sound, positioned in the second zone to measure the distance from the distance sensor to the surface of the sample in the sample container. In particular the distance sensor may be above, e.g. vertically above, the sample container when the displaceable arm is in the second position. Thereby the height of the sample in the sample container can be measured. When the sampling apparatus also comprises a vibrator capable of vibrating the sample container in the second zone the height of the sample in the sample container can be measured before vibration and after vibrating the sample, e.g. to determine the bulk density and the tapped density, respectively. It is also possible to obtain several measurement points for the height of the sample under specific conditions, e.g. with respect to frequency and duration of the vibration, in particular the height of the sample can be measured as a function of the number of "taps", or duration (in seconds) times the frequency (in hertz).

The present inventors have now surprisingly found that the flowability of a sample of particles in the mean size range of 10 μm to 500 μm with a moisture content in the range of 0.5% to 7%, e.g. a milk powder, can be estimated from a plot of the height of the sample versus the number of taps or tapping time recorded in a sampling apparatus of the invention at a vibration frequency in the range of 1 Hz to 100 kHz. Thus, in another aspect the invention relates to a method of estimating the flowability of a sample of particles, which method comprises the steps of:
- providing a sample of particles having a mean size distribution in the range of 10 µm to 500 µm and a moisture content in the range of 0.5% to 7%,
- placing the sample of organic particles in a sample container with a vibrator,
- vibrating the sample container at a frequency in the range of 1 Hz to 100 kHz,
- measuring the height of the sample in the sample container until the sample the height of the sample no longer decreases upon further vibration,
- estimating the flowability of the sample by comparing a first height measurement, an intermediate height measurement and a final height measurement.

The first height measurement may be a height measurement obtained within the initial 10% of a measuring duration corresponding to the time when the vibration is started to the time when the height of the sample no longer decreases upon further vibration. The final height measurement is the value obtained when the height of the sample no longer decreases upon further vibration. The intermediate height measurement may be any height measurement obtained between the first and the final height measurement. It is preferred that multiple intermediate height measurements are included in the comparison. In order to estimate the flowability the height of the sample, optionally normalised in any desirable way, is plotted against the time of vibration, which is optionally normalised, and the flowability calculated from the measured data, e.g. as presented in the plot. The flowability may be estimated from the data using any calculation. For example, the flowabilty can be presented as the time for reaching 50% of maximal compaction of a sample, $t_{50\%}$, or the time to reach any other relative height of the sample, or a combination of times to reach certain heights of the sample. The final height, i.e. the tapped height, may also be included in the estimate, e.g. as an absolute value or as a relative value.

The method of estimating the flowability of a sample of particles can advantageously be performed without placing a weight on the sample, so that it can be performed directly in the sampling apparatus of the invention. A weight has been employed in the prior art to keep a sample flat. However, when the method of the invention was performed without positioning a weight on the sample, no adverse effect was observed on the results. Thus, in a preferred embodiment the measurements are obtained without using a weight on the sample, e.g. without positioning a weight on the sample. In a preferred embodiment the method of estimating the flowability of a sample of particles is performed in the sampling apparatus of the invention. However, the method of the invention is not limited to being performed in a sampling apparatus of the invention, and in another aspect the invention relates to an apparatus for estimating the flowability of a sample of particles as defined above. The apparatus comprises a sample container, e.g. a cylindrical sample container, a laser device having a laser sensor for recording the height of a sample in the sample container, and a vibrator for vibrating the sample container. The apparatus for estimating the flowability of a sample may also comprise a weighing cell. All details for any feature of the apparatus for estimating the flowability of a sample may be as discussed throughout this document for corresponding features of the sampling apparatus of the invention.

The method can moreover be performed in less than 1 minute, e.g. due to the high frequency. In an embodiment the vibration has an amplitude of less than 2 mm, e.g. about 1 mm or less, but despite the low amplitude the method could be performed with a measuring duration of less than 1 minute. For example, in a specific embodiment the measuring duration is in the range of 10 seconds to 40 seconds, e.g. the measuring duration is about 20 seconds or about 30 seconds. During the measuring duration the sample of particles will already have reached the final, "tapped" height, in spite of the light weight and small size of the particles, i.e. particles having a mean size distribution in the range of 10 µm to 500 µm and a moisture content in the range of 0.5% to 7%, and when the method is repeated with identical samples, e.g. a larger sample obtained in a vertical dryer and distributed into smaller subsamples for discrete analyses, the same results were found with respect to the final height of the samples and their respective flowabilities.

In a certain embodiment the sample container has a frustoconical or conical shape with the wider end representing the inlet and the narrow end representing the bottom of the sample container. When an image of a frustoconical or conical sample container filled with sample is recorded a larger proportion of the particles is available for image analysis than for a cylindrical sample container.

In a further aspect the invention relates to a dryer, e.g. a vertical dryer for producing particles having a mean size of up to 500 µm in diameter and a moisture content in the range of 0.5% to 7%, which vertical dryer comprises a drying chamber having an upper end and a lower end, an inlet for a for a liquid feed to be dried and an outlet for dried particles at the lower end of the drying chamber, and a sampling apparatus according to any embodiment of the invention, wherein the first zone is within the outlet duct of the drying chamber. In a specific embodiment the interface between the first zone and the second zone is located at a distance of up to 20% of the distance between the inlet for a liquid feed of particles and the outlet for the dried particles, as calculated from the outlet for the dried particles.

BRIEF DESCRIPTION OF THE DRAWINGS

The invention will be described in more detail below by means of non-limiting examples of presently preferred embodiments and with reference to the schematic drawings, in which

FIG. 7 shows images from a sampling apparatus;

DETAILED DESCRIPTION OF EMBODIMENTS OF THE INVENTION

Figure 1:
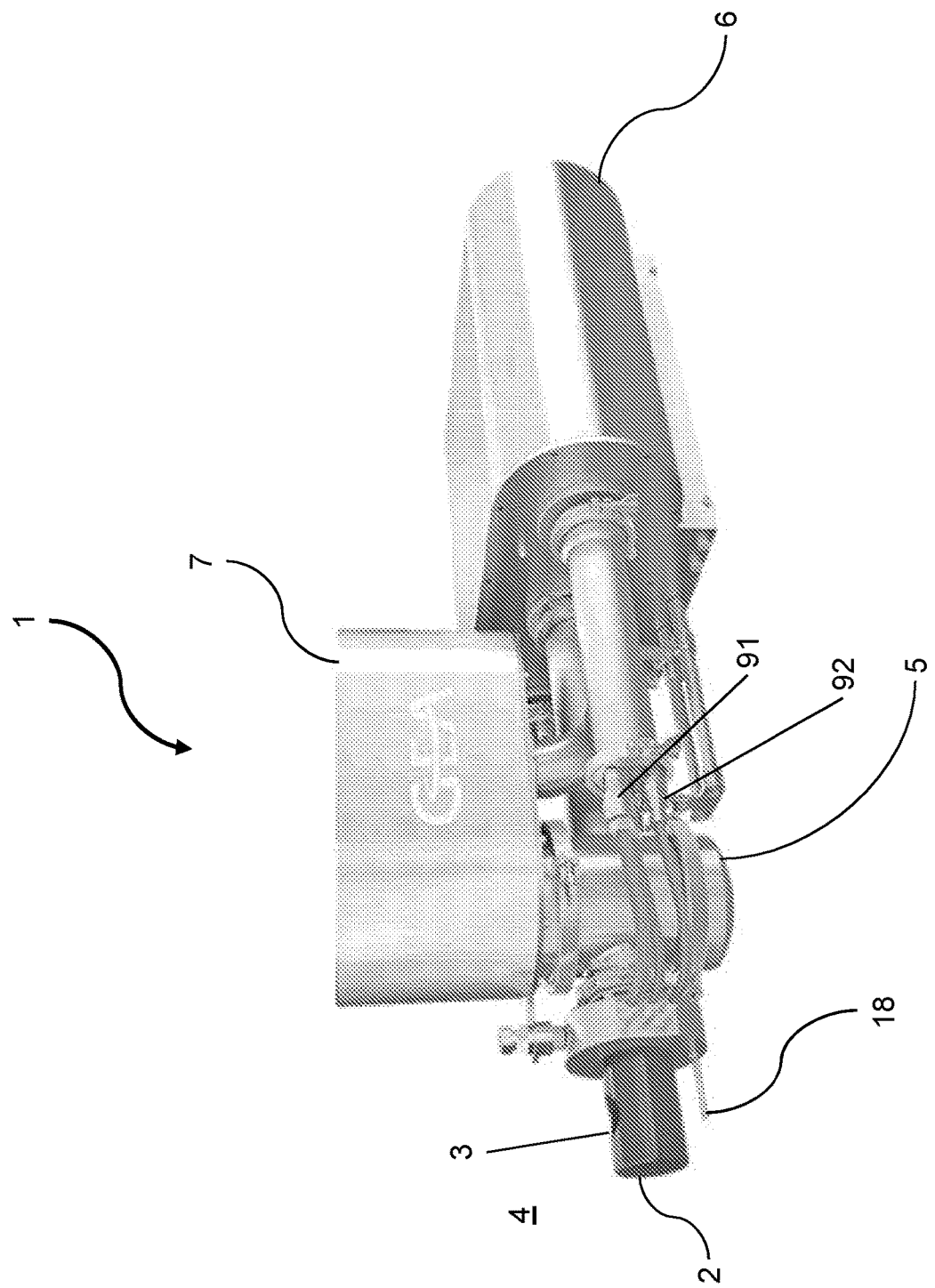
FIG. 1 shows a perspective view of a sampling apparatus in an embodiment of the present invention.
Figure 2:
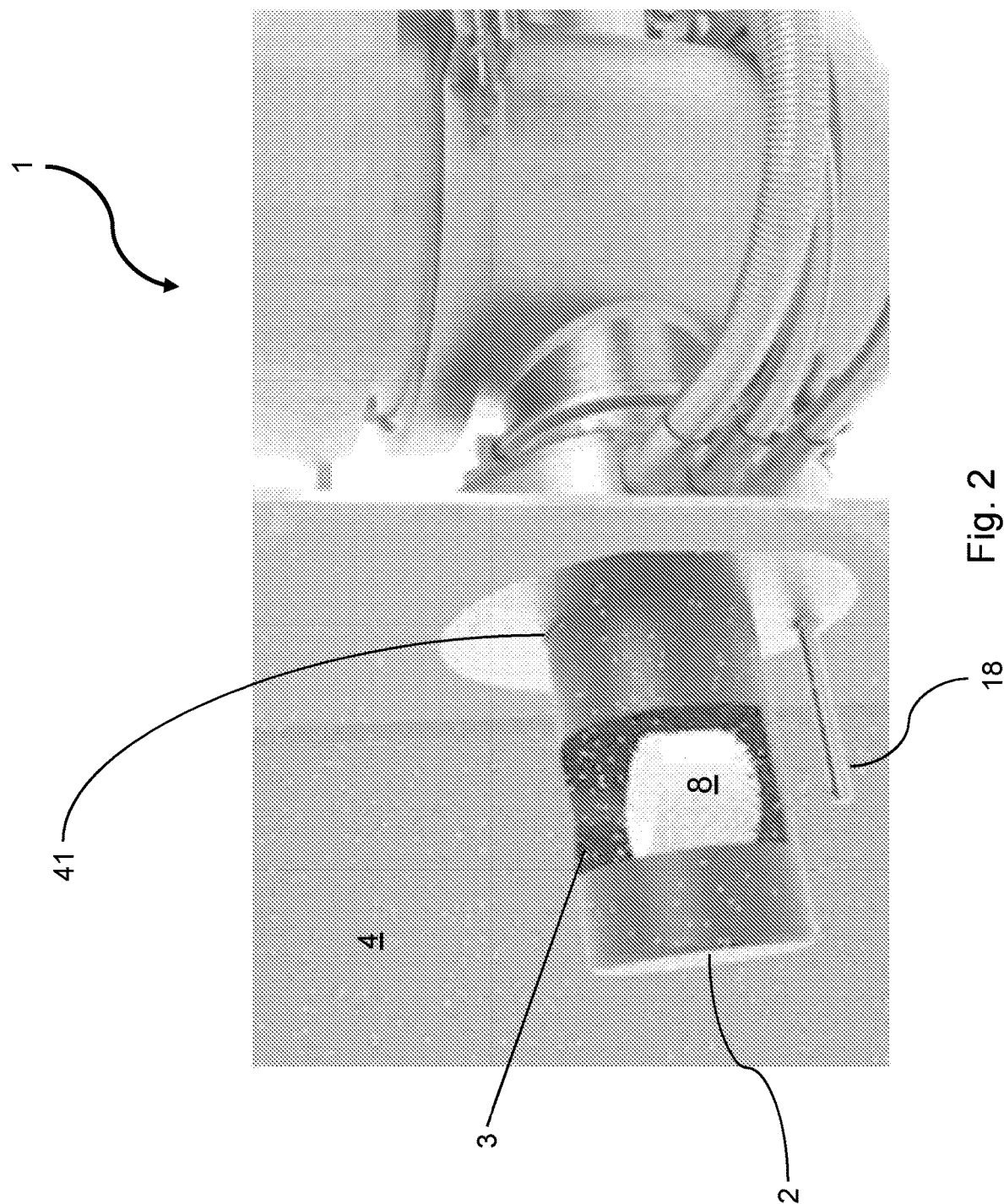
FIG. 2 shows a partial perspective view of the sample container of a sampling apparatus of the invention while being filled with a sample.

FIG. 1 shows a perspective view of a sampling apparatus 1 in an embodiment of the present invention. The sampling apparatus 1 has a displaceable arm 2 extendable along an axis from a machine housing 6 into a product stream (not shown) in a first zone 4. Thus the displaceable arm 2 with a sample container 3 is in the first position. In the second position (not shown) the displaceable arm 2, in particular the part of the displaceable arm 2 with the sample container 3 will be withdrawn into the second zone 5 where a sample (not shown) in the sample container 3 can be analysed with one or more devices for analysing a physical or chemical characteristic of the sample, which devices are located in the instrument housing 7. The sampling apparatus 1 has an air knife (not shown) in the interface between the first zone 4 and the second zone 5. The air knife is provided with compressed air from an air inlet tube 91, and the air of the air knife may be removed using the air outlet tube 92. An air knife with an air inlet tube 91 and an air outlet tube 92 is especially relevant when the air knife operates under a laminar flow. However, in other embodiments the air outlet tube 92 may also serve as an air inlet to the air knife, e.g. to provide air at several inlets to form the air knife. In FIG. 2 the displaceable arm 2 is extended to the first position through an opening 41 into the first zone 4 where a sample 8, presented as a white powder, which may be a milk powder in or from a vertical dryer, is collected in the sample container 3. Also shown is an air nozzle 18 of a device for cleaning the sample container.

Figure 3:
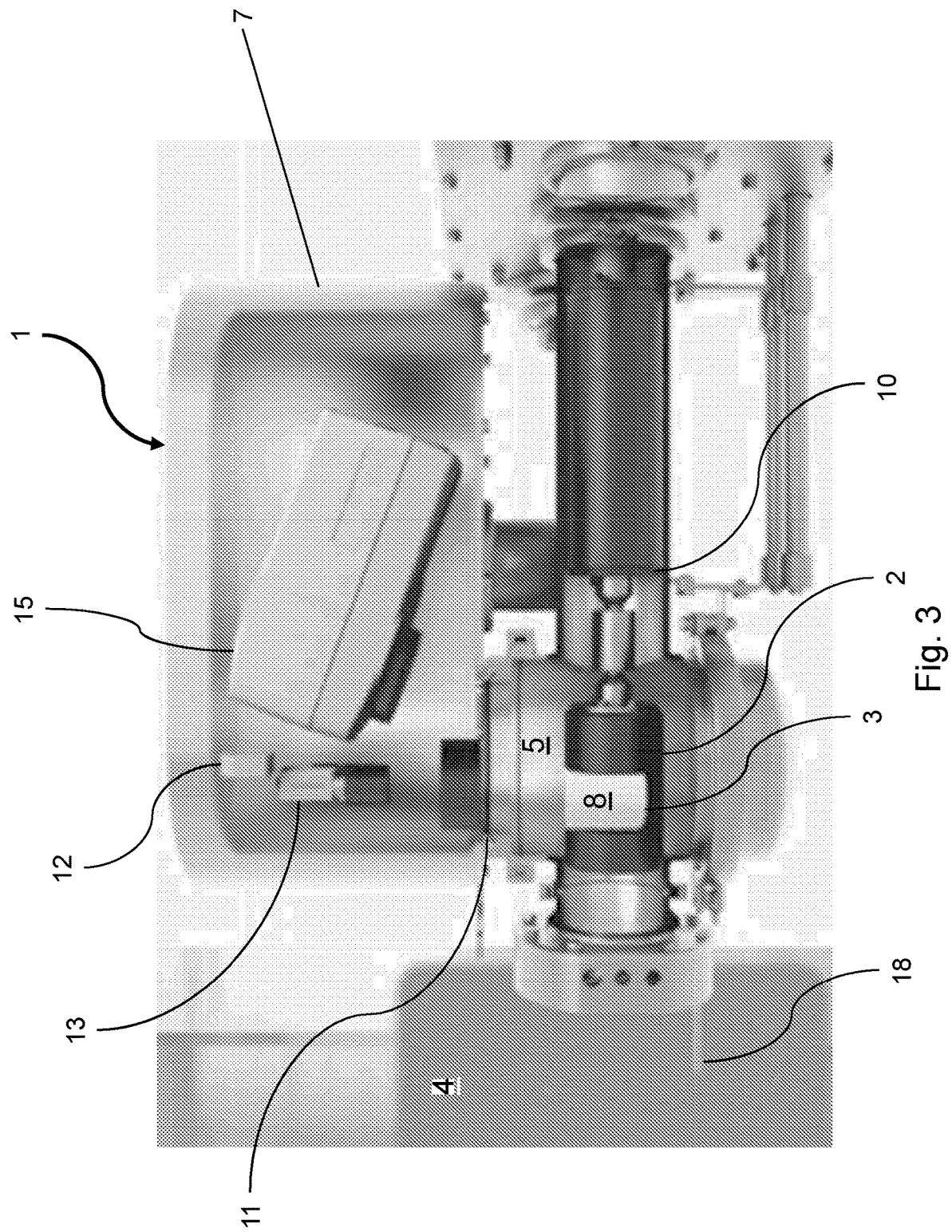
FIG. 3 shows a cross-section of an embodiment of a sampling apparatus.

FIG. 3 shows a cross-section of an embodiment of a sampling apparatus 1 of the invention. The displaceable arm 2 is in the second position in the second zone 5 where the sample 8 can be analysed by devices for analysing a physical or chemical characteristic. Specifically the height of the sample 8 can be measured with the laser device 12, photos can be recorded and analysed using the vision system 13, and the NIR scanner 15 can analyse the sample 8 for fat, protein and/or moisture. The laser device 12, the vision system 13 and the NIR scanner 15 are contained in an instrument housing 7, which is isolated from the second zone 5 by a window glass 11 in order to provide a safe zone within the instrument housing 7. The machine housing 6 is isolated from the second zone 5 using a double lip seal 10.

Figure 4:
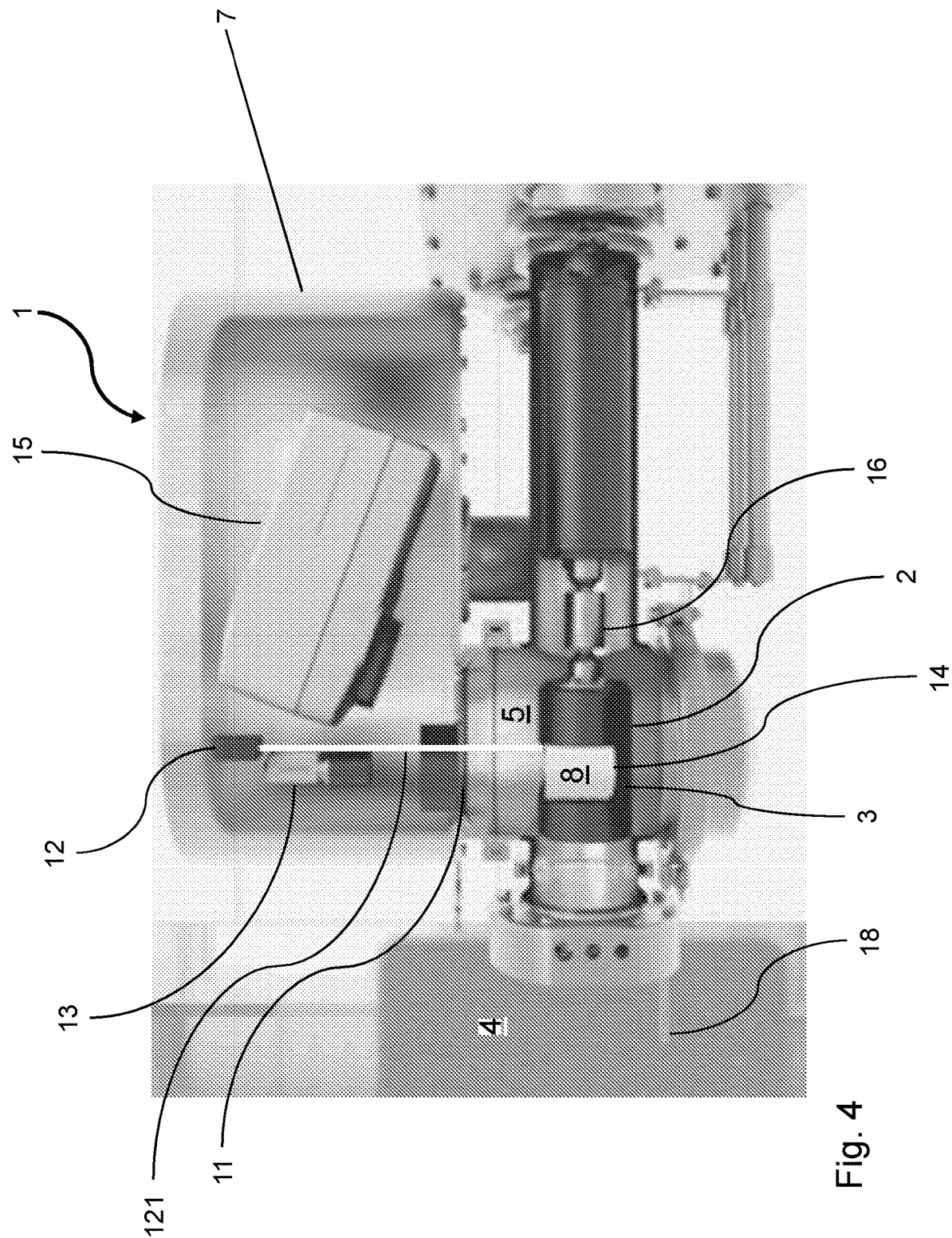
FIG. 4 shows a cross-section of an embodiment of a sampling apparatus while recording a sample height.

FIG. 4 illustrates a measurement of the height of the sample 8 using the laser device 12 where a laser beam 121 from the laser device 12 to the surface of the sample 8 is used for recording the distance between the laser device 12 and the surface of the sample 8. The sample container 3 can be vibrated using the vibrator 16 so that the sample 8 can be compacted while measuring the height of the sample 8. Thereby the tapped density of the sample 8 can be recorded and the flowability of the sample 8 estimated. The density of a sample 8 is calculated from the volume of the sample 8 as determined using the laser device 12 and the weight of the sample 8 recorded using the weighing cell 14.

Figure 5:
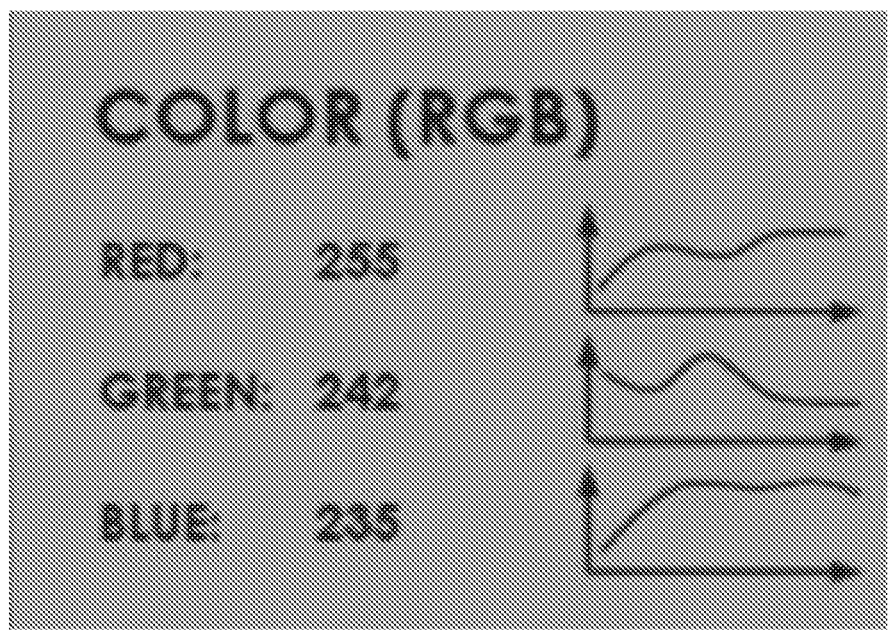
FIG. 5 shows a plot of RGB colours.

FIG. 5 shows an exemplary plot of colours in the RGB colour scheme for a point in the surface of the sample 8 as a function of sampling time. The RGB colour scheme may have an 8 bit depth for each colour, as indicated in FIG. 5, or the RGB colour scheme may employ fewer, e.g. 4 bits, or more, e.g. 12 or more, bits per colour. A colour depth of 4 bits per colour is considered sufficient for detecting a colour deviating particle.

Figure 6:
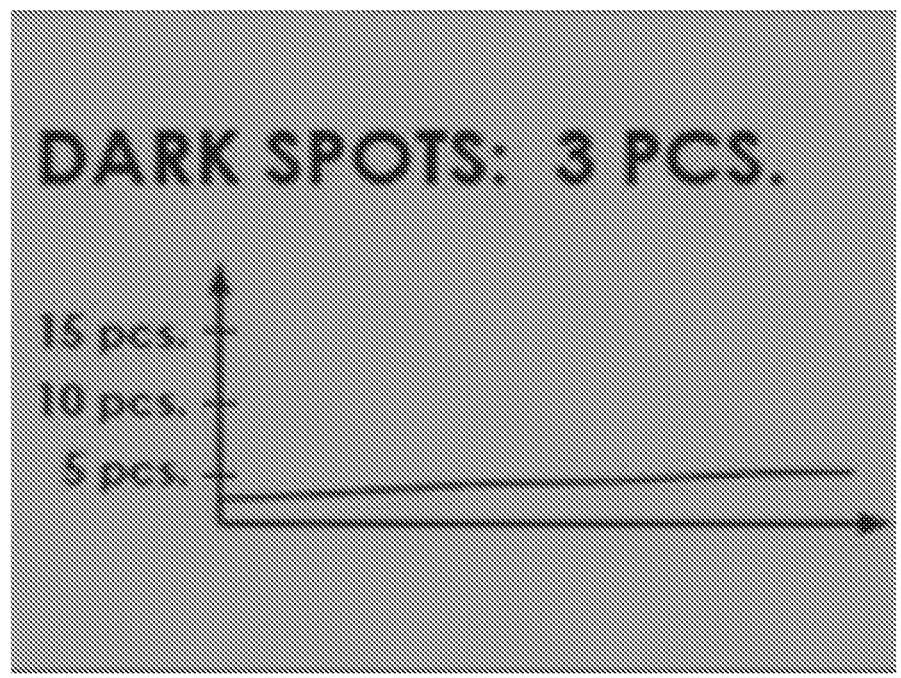
FIG. 6 shows a plot of scorched particles.

In FIG. 6 the RGB data for a sample has been converted to a quantification of scorched particles as a function of time. When a certain quantity has been reached, e.g. expressed as a percentage of dark spots in a sample, optionally quantified as scorched particles compared to the total number of particles, the sampling apparatus 1 may give an alarm. Actual images recorded in a sampling apparatus 1 of the invention are shown in FIG. 7, where the left panel shows no scorched particles and where the right panel shows visible scorched particles.

Figure 8:
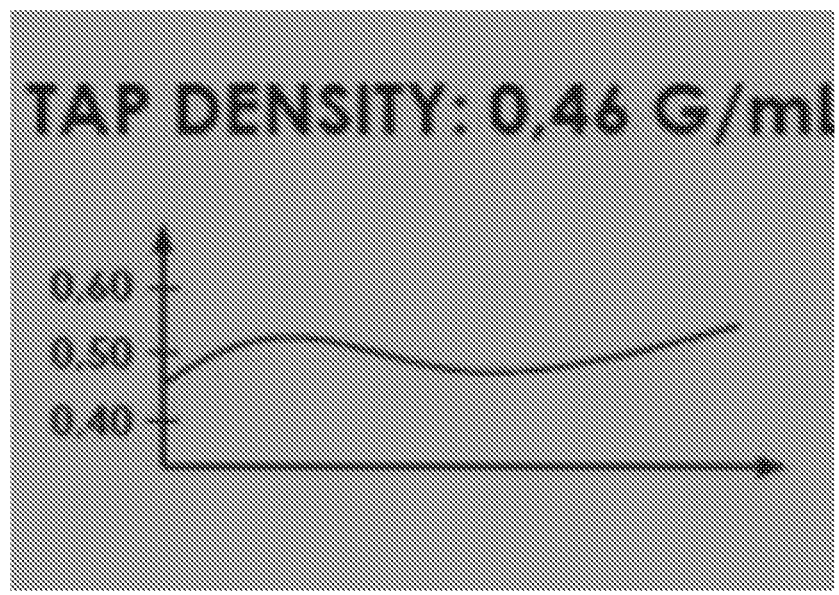
FIG. 8 shows a plot of the tapped density of samples.

FIG. 8 shows an exemplary plot of the tapped density as a function of time as recorded in a sampling apparatus 1 of the invention.

Figure 9:
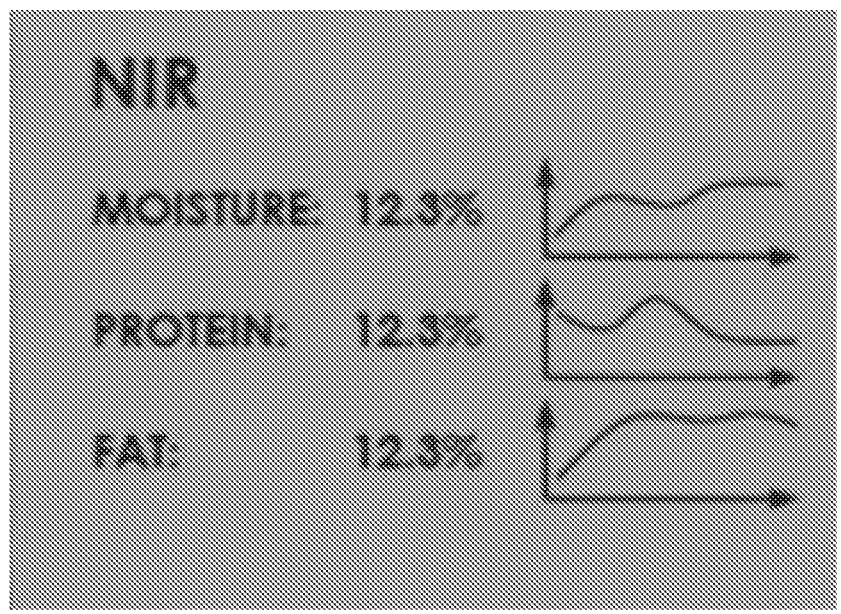
FIG. 9 shows a plot of NIR data.

FIG. 9 shows an exemplary plot of the contents of moisture, fat and protein recorded using the NIR scanner 15.

Figure 10:
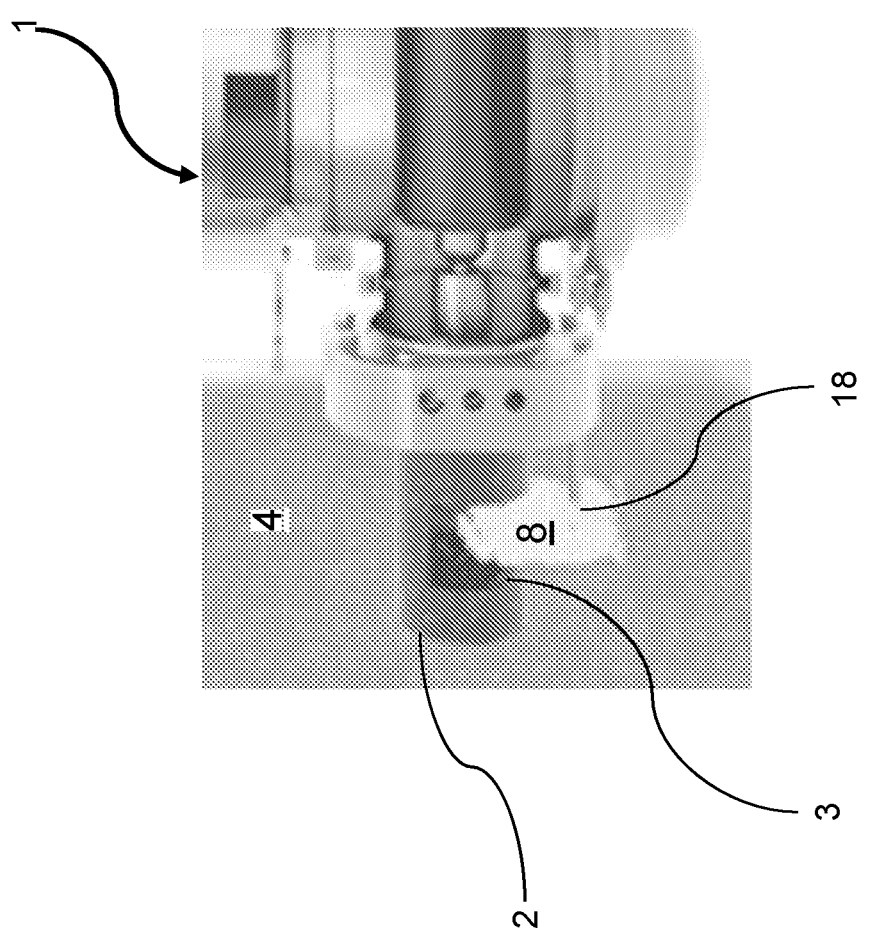
FIG. 10 shows a partial perspective view of the inverted sample container of the sampling apparatus in the first position.

FIG. 10 shows the displaceable arm 2 in the first position in the first zone 4 with the sample container 3 inverted to empty the sample 8 into the product stream.

Figure 11:
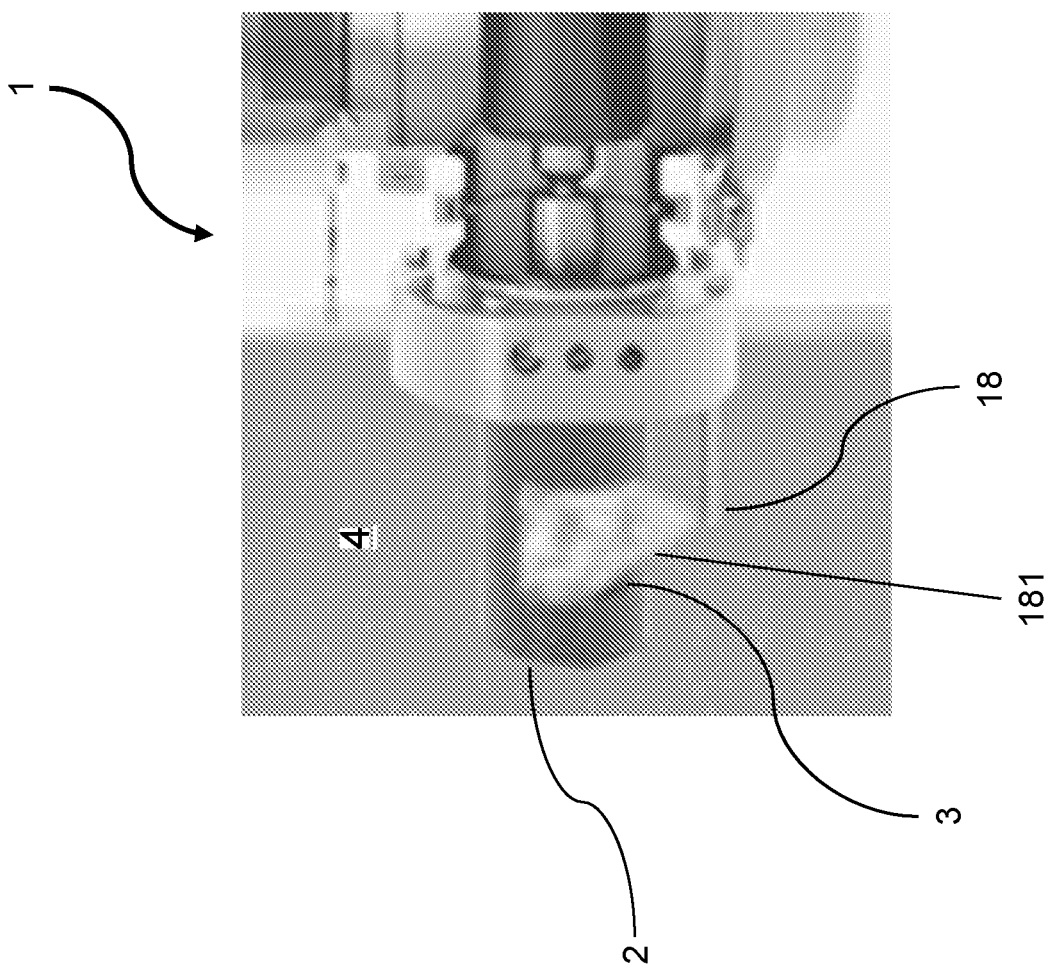
FIG. 11 is a view corresponding to FIG. 10, on a larger scale, showing the inverted sample container of the sampling apparatus in the first position.

FIG. 11 shows the displaceable arm 2 in the first position in the first zone 4 with the sample container 3 inverted and being flushed with air 181 from the air nozzle 18.

Figure 12:
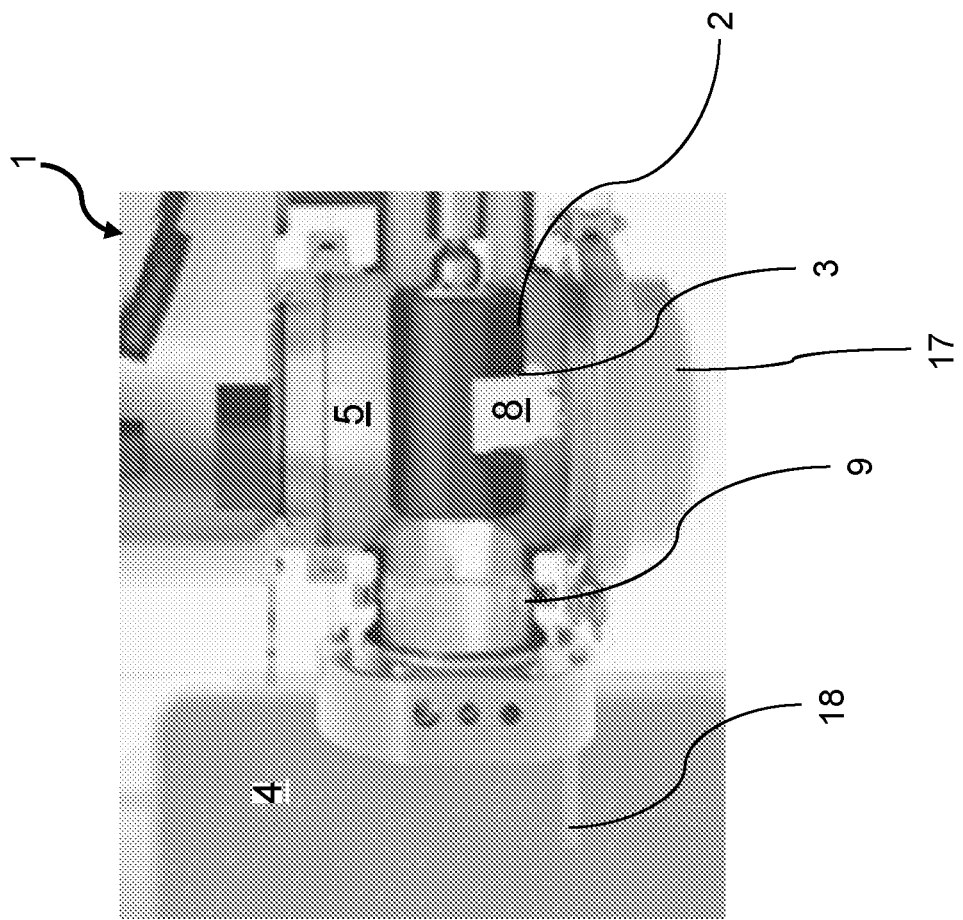
FIG. 12 is a view corresponding to FIG. 11, showing the inverted sample container of the sampling apparatus in the second position.

FIG. 12 shows the displaceable arm 2 in the second position in the second zone 5 with the sample container 3 inverted to empty the sample 8 into a verification tube 17. The first zone 4 and the second zone 5 are interfaced by an air knife 9.

Figure 13:
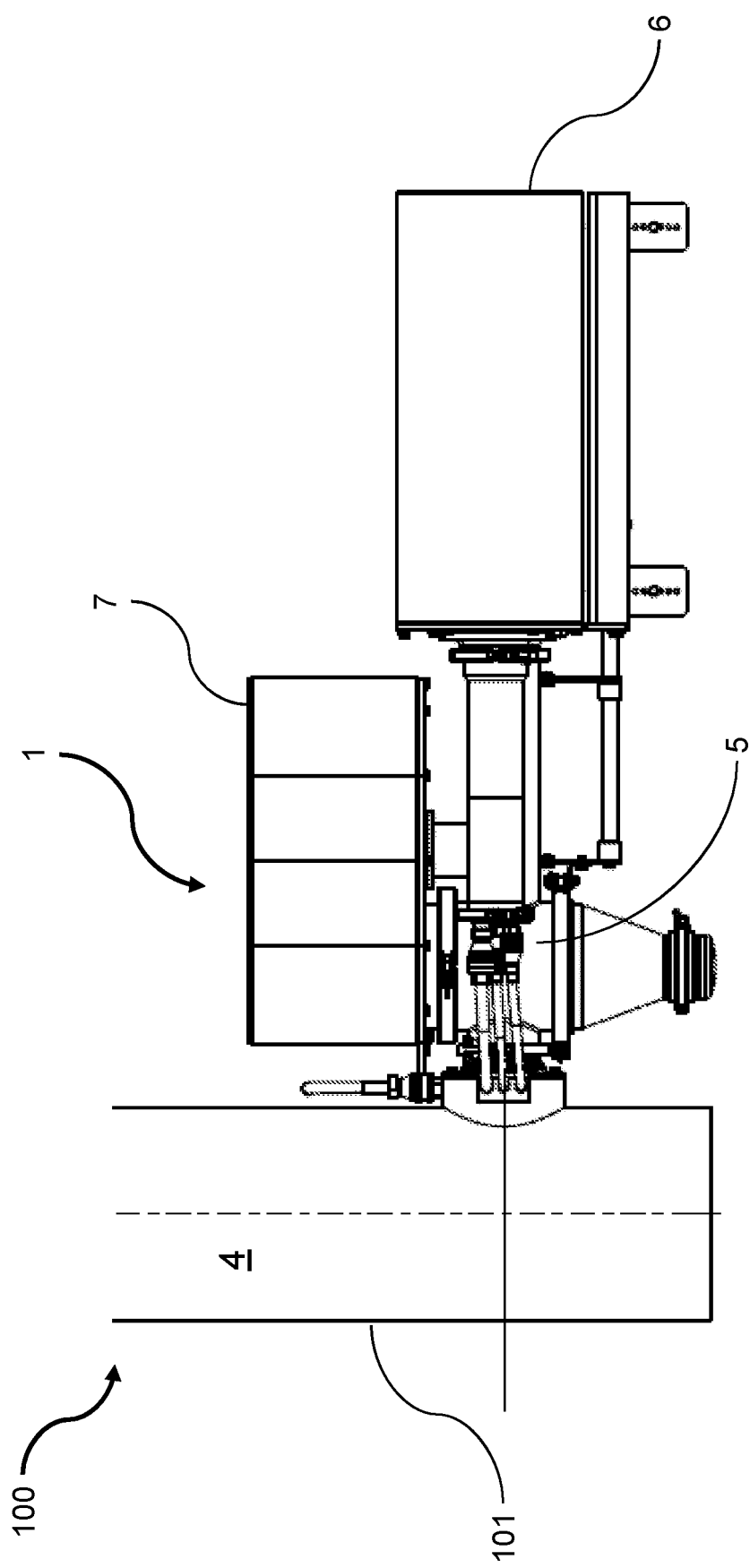
FIG. 13 is a schematic partial cross-sectional side view, showing an outlet duct from a dryer and the sampling apparatus of the invention.

FIG. 13 shows a dryer 100 of the invention comprising an outlet duct 101 connected to the sampling apparatus 1 of the invention.

Figure 14:
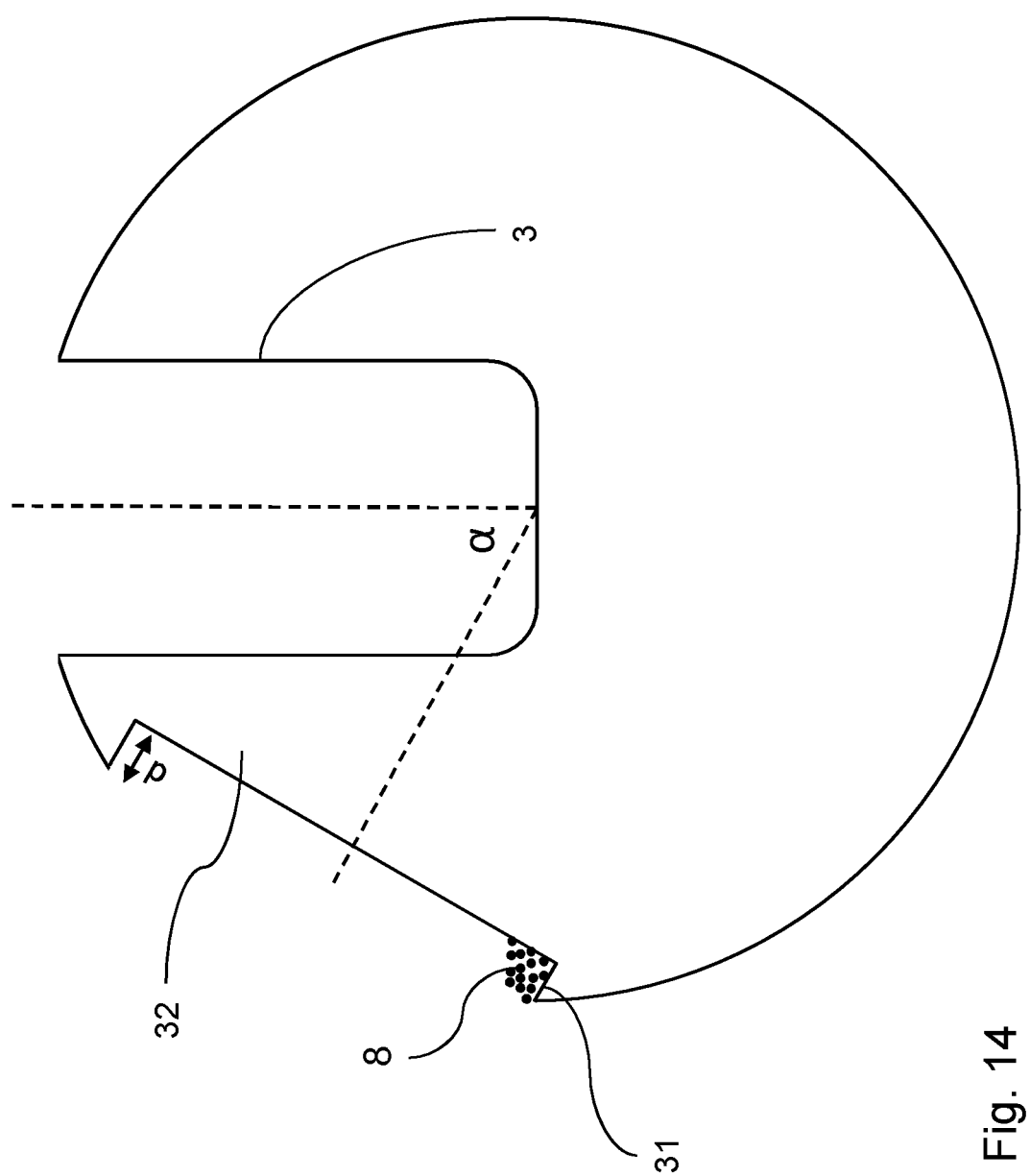
FIG. 14 is a schematic side view, showing a size sampling container in a sample collection position together with a sample container.
Figure 15:
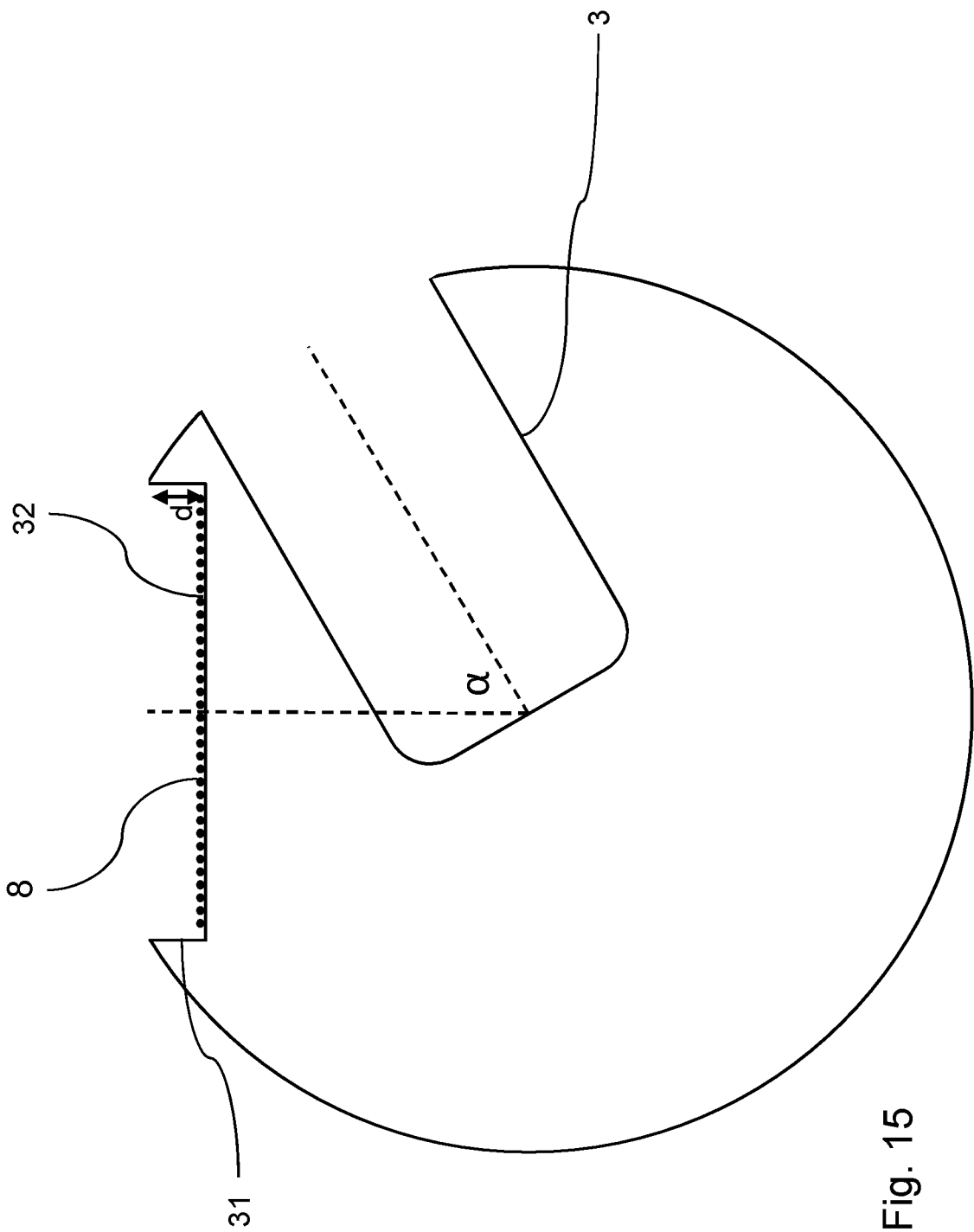
FIG. 15 is a view corresponding to FIG. 14, showing a size sampling container in a sample analysis position together with a sample container.

FIG. 14 and FIG. 15 show an embodiment of the sampling apparatus 1 of the invention where the displaceable arm (not shown in FIGS. 14 and 15) has a sample container 3 and a size sampling container 31. The angle α between the sample container 3 and the size sampling container 31 is indicated by the dotted lines. The dotted circles indicate the direction of rotation of the displaceable arm with the sample container 3 and the size sampling container 31. In FIG. 14 the displaceable arm is rotated for the size sampling container 31 to be in a position to collect a sample 8, i.e. the particle sizing position. The amount of sample 8 to be collected is limited by the angle in which the size sampling container 31 is rotated relative to the direction of the product stream (which in FIGS. 14 and 15 is vertical from top to bottom) coupled with the depth d of the size sampling container. In FIG. 15 the size sampling container 31 is rotated so that the size sampling container 31 has a horizontal bottom 32 and the sample 8 spreads over the bottom 32 of the size sampling container 31. In order to further the spreading of the sample 8 over the bottom 32 of the size sampling container 31 the displaceable arm may be vibrated. In order to further improve spreading, in particular to separate agglomerated particles, the bottom 32 of the size sampling container 31 may be subjected to ultrasound or the like. When the particles of the sample 8 are distributed over the bottom 32 of the size sampling container 31 the vision system can analyse the particle sizes of the sample 8 and also quantify the scorched particles.

Figure 16C:
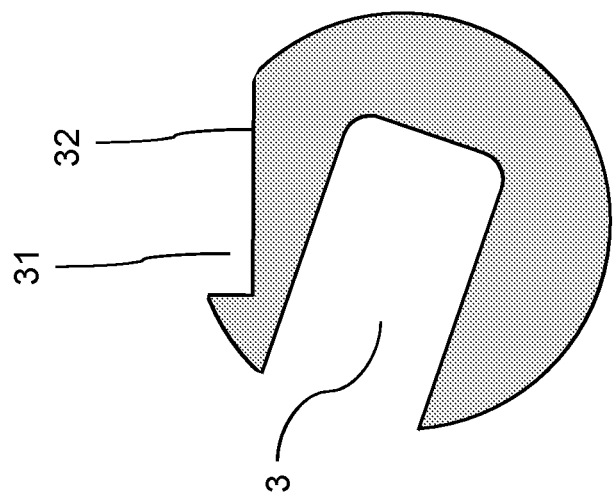
FIG. 16c is a schematic side view, showing a size sampling container and a sample container with the size sampling container in a particle analysis position.
Figure 16B:
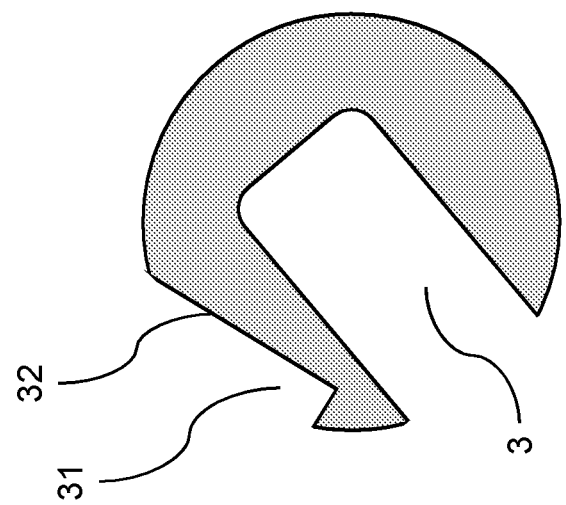
FIG. 16b is a schematic side view, showing a size sampling container and a sample container with the size sampling container in a filling position.
Figure 16A:
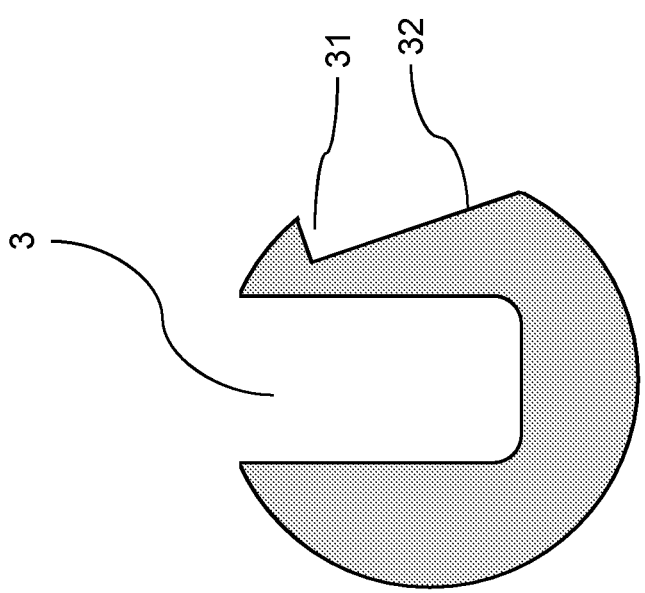
FIG. 16a is a schematic side view, showing a size sampling container and a sample container with the sample container in a filling position.

FIG. 16 shows a schematic side view of an embodiment where the displaceable arm has a sample container 3 and a size sampling container 31. In FIG. 16a the sample container 3 is rotated to be in a filling position while the size sampling container 31 will not be filled with particles. In FIG. 16b the size sampling container 31 is in a filling position while the sample container 3 will not be filled with particles. In FIG. 16c the size sampling container 31 is in a position for analysis of particles (not shown) on the bottom 32 of the size sampling container 31. In the position for analysis of particles the bottom 32 of the size sampling container 31 is horizontal.

LIST OF REFERENCE NUMERALS

1 Sampling apparatus
2 Displaceable arm
3 Sample container
31 Size sampling container
32 Bottom of size sampling container
4 First zone
41 Opening between first and second zone
5 Second zone
6 Machine housing
7 Instrument housing
8 Sample
9 Air Knife
91 Air inlet tube
92 Air outlet tube
10 Double lip seal
11 Window glass
12 Laser device
121 Laser beam
13 Vision system
14 Weighing cell
15 NIR scanner
16 Vibrator
17 Verification tube
18 Air nozzle
181 Air from the air nozzle
100 Dryer
101 Drying chamber outlet duct

The invention claimed is:

1. A sampling apparatus for explosive environments, the sampling apparatus comprising a product stream of particles of a mean size of up to 500 μm, the sampling apparatus comprising a displaceable arm having a sample container, which displaceable arm has a first position where the sample container is inserted into a first zone such that a sample of particles is collected into the sample container, and a second zone where the displaceable arm is outside the product stream, wherein the second zone is within a housing with an opening for the displaceable arm;
the sampling apparatus having an interface between the first zone and the second zone, the interface comprising one or more of a closable member, a gate valve, an air knife, a lock, or an access gate filled by the displaceable arm.

2. The sampling apparatus according to claim 1, further comprising a verification tube configured to transfer a sample in the sample container to an external site.

3. The sampling apparatus according to claim 1, wherein the housing comprises devices to monitor and adjust the pressure in the second zone.

4. The sampling apparatus according to claim 1, further comprising a device configured to clean the sample container, the device comprising an air nozzle pressurized with a medium configured to flush the sample container.

5. The sampling apparatus according to claim 1, further comprising a laser or a lamp that generates light of a desired wavelength and a sensor that detects the light of the desired wavelength.

6. The sampling apparatus according to claim 5, further comprising a data processor capable of recording and interpreting a signal from the sensor.

7. The sampling apparatus according to claim 5, further comprising a data processor capable of recording and interpreting a signal from the sensor.

8. The sampling apparatus according to claim 1, further comprising one or more of a laser scanner, a NIR scanner, a camera, or a vision system.

9. The sampling apparatus according to claim 1, further comprising a window with a window glass, wherein the window isolates the second zone such that a physical or chemical characteristic of the sample can be analyzed.

10. The sampling apparatus according to claim 1, further comprising a weighing cell.

11. The sampling apparatus according to claim 10, wherein the weighing cell is integrated in or is an integrated part of the displaceable arm.

12. The sampling apparatus according to claim 1, further comprising a vibrator.

13. The sampling apparatus according to claim 1, wherein the sample container is rotatable around an axis transverse to a direction of the product stream from which the sample is collected.

14. The sampling apparatus according to claim 13, wherein the sample container has a position to collect the sample for particle sizing, wherein when the sample container is in the position the sample container is rotated at an angle in a range of 5° to 85° from a horizontal position of the sample container.

15. The sampling apparatus according to claim 13, wherein the displaceable arm further comprises a size sampling container and wherein an angle between the sample container and the size sampling container based on the axis transverse to the direction of the product stream is in a range of 20° to 80°.

16. The sampling apparatus according to claim 1, further comprising a distance sensor positioned in the second zone to measure a distance from the distance sensor to a surface of the sample in the sample container.

17. The sampling apparatus according to claim 16, further comprising a vibrator capable of vibrating the sample container in the second zone at a frequency in a range of 1 Hz to 100 kHz and an amplitude of up to 2 mm.

18. A dryer comprising:
a drying chamber having an upper end and a lower end;
an inlet for a liquid feed to be dried;
an outlet for dried particles at the lower end of the drying chamber; and a sampling apparatus comprising:
- a product stream of particles of a mean size of up to 500 µm;
- a displaceable arm having a sample container, the displaceable arm having a first position where the sample container is inserted into a first zone such that a sample of particles is collected into the sample container, and a second zone where the displaceable arm is outside the product stream, wherein the second zone is within a housing with an opening for the displaceable arm; and
- an interface between the first zone and the second zone, the interface comprising one or more of a closable member, a gate valve, an air knife, a lock, or an access gate filled by the displaceable arm, wherein the first zone is within the drying chamber or in a duct attached thereto.

19. A method of estimating a flowability of a sample of particles, the method comprising:
- providing a sample of particles having a mean size distribution between 10 µm and 500 µm and a moisture content between 0.5% and 7%;
- placing the sample of particles in a sample container with a vibrator;
- vibrating the sample container at a first frequency between 1 Hz and 100 kHz;
- measuring a height of the sample in the sample container until the height of the sample no longer decreases upon further vibration; and
- estimating the flowability of the sample by comparing a first height measurement, an intermediate height measurement, and a final height measurement.

20. The method according to claim 19, wherein the method is performed without positioning a weight on the sample.

21. The method according to claim 19, wherein the method is performed in less than 1 minute.

22. The method according to claim 19, wherein the vibration has an amplitude of less than 2 mm.

23. The method according to claim 19, wherein the method is performed in a sampling apparatus comprising a displaceable arm having a sample container, the displaceable arm having a first position where the sample container is inserted into a first zone to collect a sample of particles into the sample container, and a second zone where the displaceable arm is outside a product stream, the second zone being contained in a housing with an opening for the displaceable arm, the sampling apparatus having an interface between the first zone and the second zone, wherein the interface comprises one or more of a closable member, a gate valve, an air knife, a lock or an access gate filled by the displaceable arm, and wherein the sampling apparatus further comprises a vibrator capable of vibrating the sample container in the second zone at a second frequency between 1 Hz and 100 kHz and an amplitude of up to 2 mm.

* * * * *